United States Patent [19]

Raghuprasad

[11] Patent Number: 5,233,988
[45] Date of Patent: Aug. 10, 1993

[54] NEURO-AID

[76] Inventor: Puthalath K. Raghuprasad, 2310 Bobwhite Dr., Odessa, Tex. 79761

[21] Appl. No.: 646,919

[22] Filed: Jan. 28, 1991

[51] Int. Cl.⁵ .............................................. A61B 5/00
[52] U.S. Cl. .................................. 128/630; 128/744; 128/745
[58] Field of Search ....................... 128/630, 744, 745

[56] References Cited

U.S. PATENT DOCUMENTS

| D. 136,273 | 8/1943 | Brandenburg . | |
|---|---|---|---|
| 2,315,160 | 3/1943 | Newstedt et al. | 128/2 |
| 2,328,700 | 9/1943 | Wiltberger . | |
| 2,678,692 | 5/1954 | Ranseen | 128/630 X |
| 2,704,539 | 3/1955 | Fisher | 128/2 |
| 2,908,268 | 10/1959 | Guest | 128/2 |
| 3,011,394 | 12/1961 | Sherman et al. | 88/20 |
| 3,344,781 | 10/1967 | Allen | 34/457 |
| 3,488,053 | 1/1970 | Patel | 273/1 |
| 3,747,589 | 7/1973 | Harrison et al. | 128/2 |
| 3,892,227 | 7/1975 | Coursin et al. | 128/2.1 B |
| 3,901,215 | 8/1975 | John | 128/1.1 B |
| 4,265,248 | 5/1981 | Chuiton et al. | 128/630 |
| 4,723,625 | 2/1988 | Komlos | 180/272 |
| 4,913,160 | 4/1990 | John | 128/731 |

Primary Examiner—Lee S. Cohen
Assistant Examiner—Kevin Pontius
Attorney, Agent, or Firm—Marcus L. Bates

[57] ABSTRACT

Neurological testing apparatus by which the sense receptor's of a person can be tested. The apparatus is of a configuration to be held in the hand and includes a body having a front surface opposed to a rear surface to provide ample space for supporting a plurality of spaced apart covered substances thereon. The substances are each different from the other and each substance test one of a person's sense receptors. One of the members include a sweet tasting substance, another member includes a sour tasting substance, and another member includes a substance fragrant to a person's smell. Other substances include color and indicia. A protective cover is removably placed on the substance for testing the smell and taste. The testing apparatus further includes a sharp end opposed to a disk end for testing a person'-sense of feel and peripheral vision.

18 Claims, 1 Drawing Sheet

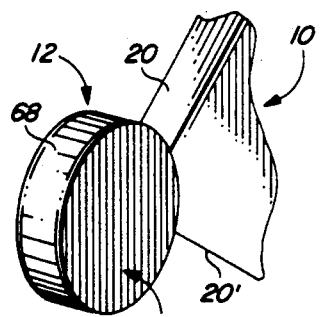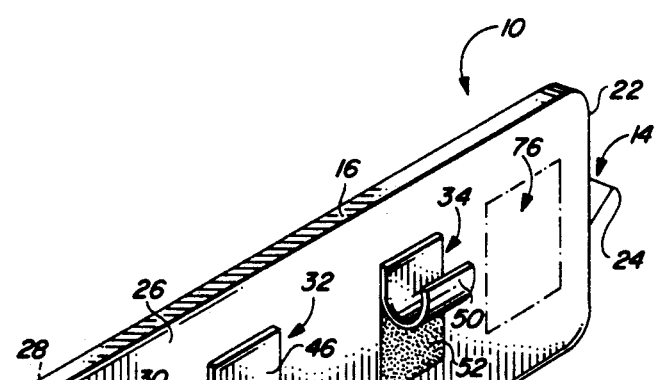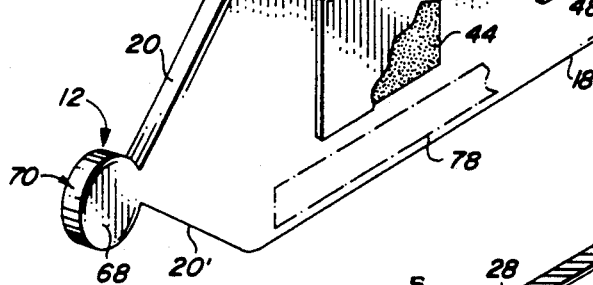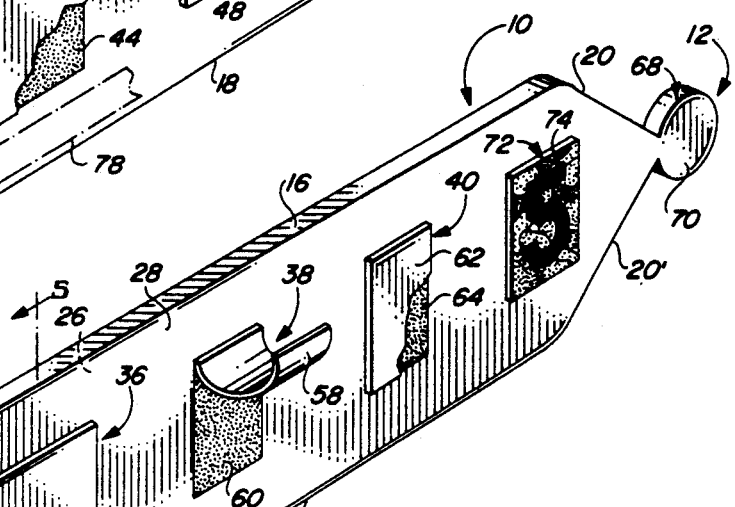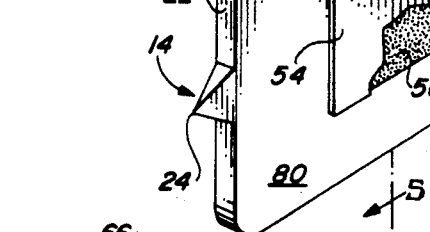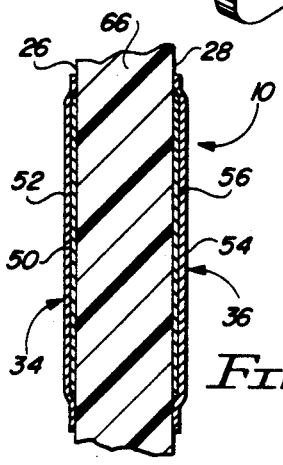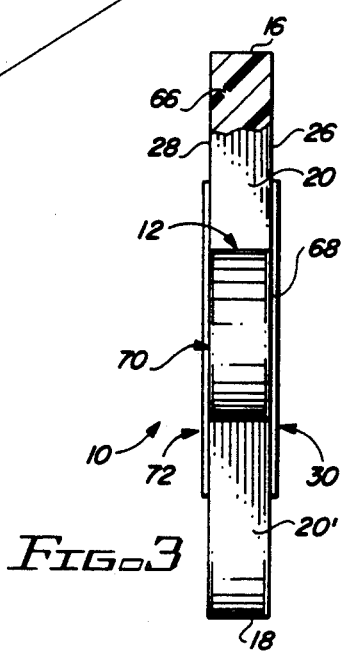

NEURO-AID

BACKGROUND OF THE INVENTION

The neurological examination is accomplished by examining, in succession, the "higher functions" (by testing memory, intelligence, orientation in time, place and person), and speech, the "cranial nerves", the motor and sensory systems, cerebellar functions and the reflexes.

In clinical practice, some of the important components of the examination include the use of various aromatic substances for testing the first cranial nerve (or the olfactory nerve); confrontation testing for the second cranial nerve (the optic nerve and the optic tract) for the field of vision, color vision and visual acuity testing with appropriate charts, again for the optic nerve and retina; touch sensation for testing sensory cranial as well as peripheral nerves by using cotton wool; pain sensation is tested by a pin prick; and the motor reflexes are tested using the tendon hammer (for eliciting the "knee and ankle jerks", and so on).

Those skilled in the art appreciate that such testing of the nervous system is involved, that it requires several separate testing"devices" and, unless the practitioner is methodical, many of the ingredients of the testing can be missed.

The present invention is designed with the express intent of providing, in one small device which can be carrie din the lab coat pocket, many of the essential ingredients for a thorough neurological examination. It is also possible to make this device entirely or partly disposable and yet essentially inexpensive, as many of the ingredients can be selected from inexpensive substances that are supported on a thin body made of plastic and adhesive tape.

SUMMARY OF THE INVENTION

This invention comprehends an inexpensive, hand held, neurological testing apparatus for testing or evaluating different aspects of the neurological system. The neurological testing apparatus comprises a body of a configuration to be held in the hand, and stored in the shirt pocket. The testing apparatus has a front surface opposed to a rear surface, with the front and rear surfaces being of a size that is defined by a top and bottom edge and opposed ends. A plurality of spaced apart members are supported at various stations on the opposed surfaces of the body, and each of the members have means associated therewith for testing at least one of the person's sense receptors. Preferably, there are ample members provided for testing all of the sense receptors at least one time.

In the preferred embodiment, a hand held, disposable, body has several members supported thereon for testing one's ability to smell, several members supported thereon for testing one's ability to taste, a member for testing a person's response to touch and pain, another member for testing peripheral vision, another member for testing color comprehension, and still another member for testing visual acuity.

Still more specifically, the various members are oriented on the opposed front and rear surfaces of the testing apparatus so that the various members that test for odors and the various members that test for taste are segregated from one another and do not interfere unduly with the operation of one another. The substances for testing taste and the substances for testing smell include a removable cover applied thereto so that each substance is protected as well as isolated. The cover can have a colored surface as well as being provided with indicia. The opposed surfaces can additionally have operational instructions printed thereon.

Accordingly, a primary object of the present invention is the provision of neurological testing apparatus by which a person's sensory receptors are selectively subjected to various substances that enable a determination of the presence of a dysfunction of the sensory receptors Another object of the invention is the provision of apparatus for testing a person's sense receptors by subjecting the appropriate sensor to a taste, smell, visual, touch and pain test.

A further object of this invention is to disclose and provide an inexpensive, hand held, disposable testing apparatus for testing a person's sense receptors by sequentially testing the person's ability to smell, taste, feel, and further including the testing of a person's vision.

A still further object of this invention is the provision of a simple, inexpensive, disposable, neurological testing apparatus by which a person's sense receptors are tested by the provision of a hand held device having a plurality of stations, with each station having a substance applied thereto, with one of the substances providing a means for testing one's taste, another of the substances providing a means for testing one's smell, and other of the substances providing a means for testing touch, vision, and color comprehension.

An additional object of the present invention is the provision of a simple, inexpensive, disposable, neurological testing apparatus by which a person's sense receptors are tested by the provision of a hand held device having a plurality of stations, with each station having a substance applied thereto, with one of the substances providing a means for testing one's taste, another of the substances providing a means for testing one's smell, and other of the substances providing a means for testing touch, vision, and color comprehension, pain, a circular member with red on one side and white on the other for testing the field of vision, and reflex testing.

These and various other objects and advantages of the invention will become readily apparent to those skilled in the art upon reading the following detailed description and claims and by referring to the accompanying drawings.

The above objects are attained in accordance with the present invention by the provision of a combination of elements which are fabricated in a manner substantially as described herein, and illustrated in the accompanying drawings.

BRIEF DESCRIPTION OF THE DRAWINGS

FIG. 1 is a perspective view of a neuro-aid testing apparatus made in accordance with the present invention;

FIG. 2 is a perspective view showing the opposite side of the neuro-aid testing apparatus of FIG. 1;

FIG. 3 is an end view of the neuro-aid testing apparatus of FIGS. 1 and 2, with some parts being broken away therefrom and the remaining parts being show in cross-section;

FIG. 4 is an opposite view of the neuro-aid testing apparatus of FIG. 3, with some parts being broken away therefrom and some of the remaining parts being shown in cross-section;

FIG. 5 is a broken, cross-sectional view taken along line 5—5 of FIG. 2.

DETAILED DESCRIPTION OF THE PREFERRED EMBODIMENT

The figures of the drawings disclose a neurological testing apparatus 10 for analyzing or testing the performance of a person's sensory receptors, comprising a body having a disk end 12 opposed to a sharp end 14, and opposed top and bottom edges 16 and 18, respectively. The top and bottom edges 16 and 18 converge at 20 and 20' toward the disk end 12. The sharp end 14 preferably has a perpendicular end 22 interrupted by a pyramid that terminates in a very sharp point 24.

The neurological testing apparatus 10 has opposed flat surfaces 26 and 28, each of which is divided into the illustrated stations 30, 32, 34, 36, 38 and 40. Each station 30-40 supports a substance thereon for testing the performance or degree of activity of one of the sensory receptors of a person.

Stations 30-40, respectively, each have a substance 44, 48, 52, 56, 60, 64, respectively, applied thereto. The substances 44-46 preferably are selected for the group comprising: a sweet tasting substance, a sour tasting substance, a salty tasting substance, a substance that emits an odor that is fragrant to a person's smell, and further including one pleasant and one unpleasant fragrance, all of which are isolated by a removable protective cover 42, 46, 50, 54, 58, and 62.

The stations preferably are grouped on opposed surfaces 26 an 28 of the body and are oriented respective to one another whereby the various substances interfere a minimal amount respective to one another. The covers, together with surface 26 or 28 encapsulates the respective substances therewithin.

In FIGS. 3, 4 and 5, numeral 6 indicates that the neuro-aid testing apparatus 10 is made of a relatively thin, plastic body that is of a size to be held in the hand, and preferably is of a substantially rectangular configuration, with the before mentioned disk 12 and sharp end 14 being opposed to one another and located along the major axis of the rectangular body.

The disk end 12 has been provided with a white color side 68 opposed to a red color side 70 for determining field of vision.

Color blindness test substance 72 is arranged to provide indicia 74 that tests one's color comprehension. Numeral 76 indicates an area which can be used for other indicia, as for example, testing the optical properties of the eye. The remaining area 78 and 80 is provided with indicia related to operating instructions of the neuro-aid testing apparatus 10.

The various stations 30-40 preferably have a substance at 44-64 made to enable the healthy person to identify an aroma or smell that is reminiscent of one of the following: coffee, roses, clothes, cinnamon. The substances 48 and 60 at stations 32 and 38 preferably trigger the tasting sensors of a healthy person and is selected from one of the following: salt, sweet, and sour. The substance can be an air drying slurry that is painted onto the station; for example, a thin layer of sweetened material of neutral smell, that is located adjacent to a sour tasting thin layer of substance having a neutral smell. Other substances that activate or trigger the taste or the smell can also be supported at 76, if desired.

Furthermore, the removable covers 42, 46, 50, 54, 58 and 62 can be made of different colors, or alternatively, can have indicia formed thereon related to data that should be comprehended by the average person and other data that can be comprehended by less capable persons. The removable covers can be thin plastic having adhesive thereon by which the cover removably adheres to the station.

In operation, testing apparatus 10 is held in the hand and the sharp point 24 used to contact the patient's skin to determine the response to touch. Testing apparatus 10 is then easily flipped to expose opposed surfaces 26 and 28, thereby exposing white or red colors at 68 and 70 in order to measure the range of a person's peripheral vision. Then a person can be tested for color blindness at station 72. Next, the person can identify numbers and colors on the surface of the various covers 42, 46, 50, 54, 58, and 62. The technician may ask the person to identify the color or the indicia formed on cover 42 as the cover is removed from the underlying substance 44. Then the person is instructed to taste the substance 44 after which the cover 42 is replaced and then the same technique is used at the remaining stations by alternately testing the person's ability to identify the color, indicia, taste, and then smell.

The testing apparatus 10 can be made by injection molding or alternatively can be stamped form an endless sheet of thin, flexible, solid material including heavy paper and plastic.

Where testing apparatus 10 is injected molded, the disk end 12 can be made any desired diameter and provided with appropriate colored sides, with the opposed sharp point 24 being a pyramid such as seen in FIG. 4. The injection molded apparatus can have either cavities or other physically defined stations 30-40 formed thereon.

In a simpler and highly useful embodiment, the disk end 12 and the sharp point 24 end is a continuation of surfaces 26, 28. In the embodiment of FIGS. 1-4, testing apparatus 10 preferably is a thin, flexible, piece of plastic made from stamping or cutting from a continuous length of plastic material, after which the various substances and covers are applied to opposed surfaces 26, 28 in the manner illustrated in the drawings.

The length and height of testing apparatus 10 can be changed to accommodate the number of stations, but preferably is of rectangular configuration, made from a thin, flexible, piece of commercially available self supporting material, such as heavy paper or plastic material, that is easily stamped or cut into the illustrated configuration of the drawings. The manufacturing cost of testing apparatus 10 should be nominal and therefore it can be discarded after use.

I claim:

1. Neurological testing apparatus for analyzing a person's sense receptors comprising a body having opposed flat surfaces to provide a rear support surface opposed to a front support surface, the opposed surfaces terminating at top and bottom edges and opposed ends;

a plurality of different substances for testing various ones of a person'sense receptors; said substances being selected from the group consisting of: a sweet tasting substance, a sour tasting substance, a salty tasting substance, and a substance having an odor that is fragrant to a person'smell;

one said surface is divided into a plurality of spaced stations, each station supports one of said plurality of different substances thereon in fixed relationship respective to the one said surface, each station having a different substance thereon for testing a selected sense receptor;

means encapsulating each said substance to isolate the substance of one station form the substance of an adjacent station to thereby enable a person to be sequentially subjected to any selected one of the substances of each of the stations and thereby test the ability of a person to utilize his sense receptors.

2. The neurological testing apparatus of claim 1 wherein one end of said body terminates in a sharp point for testing the response to touch, and the opposed end has means forming a disk at the marginal end thereof, by which a red color is applied to one side of said disk and a white color to the side opposed thereto for determining field of vision.

3. The neurological testing apparatus of claim 1 wherein said means encapsulating each said substance is a removable protective cover superimposed on each said substance for isolating the substance of selected stations and thereby make the substance available for testing the person's senses only upon removing the cover.

4. The neurological testing apparatus of claim 1 wherein the plurality of said spaced stations is supported on said front and rear support surfaces;
said means encapsulating each said substance is a cover that is removably applied to the station in superimposed relationship respective to the substance thereof and is removed to expose the substance to a person's senses, and thereafter the cover can be replaced to again isolate the substance.

5. The neurological testing apparatus of claim 1 wherein said body is an elongated, flexible, relatively thin, substantially rectangular member having a sharp end opposed to a disk end; said sharp end can be used to prick the skin and thereby test the person's sense of touch, means providing a red color on one side of said disk end and a white color on the side opposite to the red color side, whereby said disk end can be used for testing a person's field of vision.

6. The neurological testing apparatus of claim 5 wherein said means encapsulating each said substance is a removable protective cover superimposed over the substance of a station for isolating the substances from one another whereby the substance is made available to the senses only upon removing the cover.

7. The neurological testing apparatus of claim 1 wherein there is further included in said encapsulating means a removable protective cover for isolating a substance at selected stations whereby the substance is made available to the senses only upon removing the cover; and further including a station having means forming colored indicia thereon for evaluating color blindness.

8. Disposable apparatus for testing the sense receptors of a person, said apparatus comprising a body of a configuration to be held in the hand; said body is a relatively thin member having a front surface opposed to a rear surface, a plurality of spaced apart stations on said front surface,
a substance affixed to and supported on said body at each said station, each said substance is of a composition for testing one of a plurality of a person's sense receptors;
one of said substances includes a sweet tasting substance, another of said substances includes sour tasting substance, another of said substances includes a salty tasting substance, another of said substances includes means by which an odor is emitted that is fragrant to a person's smell;
and means for sequentially subjecting a person to a selected substance at each said station and thereby ascertain the efficiency of a person's sense receptors.

9. The apparatus of claim 8 wherein there is a station having means forming colored indicia thereon by which color blindness can be tested;
a marginal end of opposed surfaces of the body has means for ascertaining the person's field of vision by which a red color is applied to one side thereof and a white color to the other side thereof.

10. The apparatus of claim 8 wherein said means for sequentially subjecting a person to a selected substance at each said station includes a removable protective cover superimposed upon selected substances for encapsulating each of the selected substances and isolating one from the other whereby the selected substance is made available to the senses only upon removing the cover.

11. The apparatus of claim 8 wherein there is a plurality of said substances supported on said front and rear surfaces for testing a plurality of sense receptors;
each said substance is directly affixed in supported relationship on a surface; the means for sequentially subjecting include a cover for isolating each said substance from an adjacent substance, said cover is removably applied in superimposed relationship respective to the substance and is removed to expose the substance to a person's sense receptors.

12. The apparatus of claim 8 wherein said body is an elongated, flexible, relatively thin, rectangular member having a sharp terminal end opposed to a curved terminal end; said sharp terminal end is used to prick the skin and to scratch the skin to determine a persons' reflexes, while said curved end is used to support a red color on one surface thereof and a white color on the opposed surface thereof for testing a person's visual acuity.

13. The apparatus of claim 12 wherein said means for sequentially subjecting a person to a selected substance at each said station includes a removable protective cover for encapsulating selected substances whereby the substance is made available to the senses only upon removing the cover.

14. The apparatus of claim 8 wherein said means for sequentially subjecting a person to a selected substance at each said station includes a protective cover removably affixed to a station in superimposed relationship respective to the substance thereof to thereby encapsulate and isolate selected substances, whereby the substance is made available to the senses only upon removing the cover;
and further including means forming colored indicia at a station that is related to numbers for evaluating a persons' degree of color blindness.

15. The apparatus of claim 12 wherein said body is an elongated, flexible, relatively thin, rectangular member that terminates in a sharp terminal end that is opposed to a curved marginal terminal end; said sharp end is used to prick the skin and test reflexes; said curved marginal end is used to support a red substance on one surface thereof and a white substance on the surface opposed thereto for testing a person's field of vision;
said means for sequentially subjecting a person to a selected substance includes a removable protective cover applied to selected substances and superimposed upon a substance for isolating each of the selected substances form an adjacent substance, whereby the selected substance is made available to the senses only upon removing the cover.

16. Apparatus for evaluating the response of the sense receptors of a person comprising a body of a configuration to be held in the hand; said body has a front surface opposed to a rear surface;

said body is an elongated, flexible, relatively thin, rectangular member having a sharp end opposed to a curved end; said sharp end is used to test the skin while said curved end is used to support a red color on one surface thereof and a white color on the opposed surface thereof for testing a person's field of vision;

a plurality of spaced apart stations on one said surface, a substance affixed to each said station, each substance is for testing one of a person's sense receptors; one said substance includes a sweet tasting substance, another said substance is a sour tasting substance, another said substance is a salty tasting substance, another said substance emits an odor;

said substance that emits an odor is supported on one said surface opposed to the substances for testing the sense of taste;

whereby; a person can be sequentially subjected to each said substance of each said station and thereby ascertain the efficiency of a person's sensory system.

17. The apparatus of claim 16 wherein there is further included a removable protective cover for isolating selected substances whereby the substance is made available to the senses only upon removing the cover.

18. The apparatus of claim 16 wherein there is further included a removable protective cover for encapsulating selected substances whereby the selected substances are made available to the senses only upon removing the cover; one said station having means forming colored indicia thereon that is related to numerals for evaluating the degree of color blindness.

* * * * *